United States Patent [19]

Petruck et al.

[11] Patent Number: 4,570,023

[45] Date of Patent: Feb. 11, 1986

[54] PROCESS FOR THE PREPARATION OF TRICHLOROBENZENES

[75] Inventors: Gerd-Michael Petruck, Erkrath; Raimund Wambach; Adolf Wissner, both of Leverkusen; Sigurd Hartung, Cologne, all of Fed. Rep. of Germany

[73] Assignee: Bayer Aktiengesellschaft, Leverkusen, Fed. Rep. of Germany

[21] Appl. No.: 247,411

[22] Filed: Mar. 25, 1981

[30] Foreign Application Priority Data

Apr. 10, 1980 [DE] Fed. Rep. of Germany ....... 3013888

[51] Int. Cl.$^4$ ............................................. C07C 21/24
[52] U.S. Cl. .................................... 570/210; 570/207; 570/208
[58] Field of Search ......................... 570/207, 208, 210

[56] References Cited

U.S. PATENT DOCUMENTS

| | | | |
|---|---|---|---|
| 1,923,419 | 8/1981 | Britton et al. | 570/208 |
| 1,934,675 | 11/1933 | Mills | 570/208 |
| 2,123,857 | 7/1938 | Wibaut et al. | 570/207 |
| 2,843,637 | 7/1958 | Clarke et al. | 570/207 |

FOREIGN PATENT DOCUMENTS 1618517 6/1967 Fed. Rep. of Germany ...... 570/208

OTHER PUBLICATIONS

Houben-Weyl, "Methoden der Organischen Chemie", vol. 5, No. 3, pp. 656–658 (1952).
Erykalov et al., "Chemical Abstracts", vol. 63, p. 9770 (1965).
Erykalov et al, "Chemical Abstracts", vol. 59, p. 418 (1963).

*Primary Examiner*—Robert V. Hines
*Attorney, Agent, or Firm*—Sprung Horn Kramer & Woods

[57] ABSTRACT

A process for the preparation of a trichlorobenzene by chlorination of o-dichlorobenzene in the presence of a catalyst is disclosed. The catalyst comprises aluminum chloride. Preferably an iron or iron chloride containing aluminum chloride catalyst is employed.

1 Claim, No Drawings

PROCESS FOR THE PREPARATION OF TRICHLOROBENZENES

The invention relates to a process for the preparation of trichlorobenzenes having a particularly high content of 1,2,3-trichlorobenzene, by chlorinating o-dichlorobenzene in the presence of a catalyst which contains aluminum chloride.

Within the scope of the present invention, trichlorobenzenes are isomeric trichlorobenzenes, essentially 1,2,3- and 1,2,4-trichlorobenzene.

It is known to prepare trichlorobenzenes by chlorinating o-dichlorobenzene in the presence of finely divided iron or iron-(III) chloride (BIOS Final Report 986, 404; Houben-Weyl, volume V/3, 656 (1962); Japanese Patent Specification 53/2329).

A process for the preparation of trichlorobenzenes by chlorinating o-dichlorobenzene in the presence of a catalyst has been found, which is characterised in that the catalyst contains aluminum chloride.

The process according to the invention can be illustrated with the aid of the following equation:

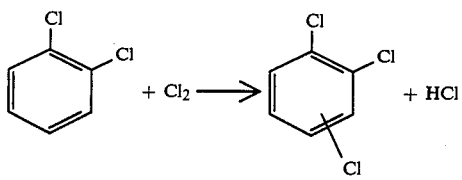

In general, anhydrous commercial aluminum chloride can be used as the aluminum chloride for the process according to the invention. Slight amounts of moisture in the aluminum chloride (up to about 2%) have no influence on the catalytic action of the catalyst. The preparation of the aluminum chloride catalyst is in itself known (Ullmanns Enzyklopädie der technischen Chemie (Ullmann's Encyclopaedia of Industrial Chemistry), volume 7, 339 (1974)).

The catalyst can be prepared, for example, by chlorinating liquid aluminum at 750°–800° C. in ceramic-lined iron chambers.

An aluminum chloride catalyst which contains small amounts of iron is preferred for the process according to the invention. Under the conditions according to the invention, iron, is as a rule, present as the chloride.

An aluminium chloride catalyst which contains 0.01 to 10 parts by weight of iron or iron chloride, relative to 100 parts by weight of aluminum chloride, is particularly preferred for the process according to the invention. An aluminum chloride catalyst which contains 0.01 to 1.0 part by weight of iron or iron chloride, relative to 100 parts by weight of aluminum chloride, is especially preferred.

According to the invention, the catalyst is employed in an amount of 0.1 to 10.0 parts by weight, preferably of 0.5 to 1.0 part by weight, relative to 100 parts by weight of the o-dichlorobenzene.

In general the chlorine is introduced in about equivalent amounts with respect to the o-dichlorobenzene.

The process according to the invention is in general carried out in the temperature range of 20° to 120° C., preferably of 20° to 50° C.

The process according to the invention is in general carried out in the pressure range of 0.1 to 10 bar, preferably at atmospheric pressure. It is as well preferred to carry out the reaction in a closed vessel at autogenous pressure.

According to the invention, the chlorination is carried out by reacting o-dichlorobenzene with elementary chlorine. The course of the reaction can be followed by, for example, measuring the density.

The process according to the invention can be carried out either discontinuously or continuously.

For example, the process according to the invention can be carried out as follows:

The o-dichlorobenzene and the catalyst are introduced into the reaction vessel and the chlorine is passed in until a certain density is reached. After completion of the reaction, the chlorination product is neutralised, for example with sodium carbonate, washed with water and distilled in vacuo. A mixture which essentially contains 1,2,3-trichlorobenzene and 1,2,4-trichlorobenzene is obtained; the two isomers can be separated by fractional distillation in the usual manner.

In a particular embodiment of the process according to the invention, the reaction is only carried out partially and the trichlorobenzenes are thus obtained with high selectivity. It is preferred to react only 20 to 95%, especially preferentially 40 to 85%, of the o-dichlorobenzene employed.

Surprisingly, the yield and selectivity of 1,2,3-trichlorobenzene achieved in chlorinating o-dichlorobenzene are increased by means of the process according to the invention. The proportion of by-products, in particular more highly chlorinated benzenes, is very low.

The trichlorobenzene prepared by the process according to the invention contains a particularly high proportion of 1,2,3-trichlorobenzene, 1,2,3-trichlorobenzene can be particularly advantageously obtained therefrom, free from its isomers, by simple physical methods of separation.

However, it is also possible to use the isomer mixture, obtained from the reaction, direct, for example as a dielectric liquid (DE-OS (German Published Specification) No. 2,920,027).

EXAMPLES 1 to 5

Chlorine is passed into 735 g (5 mols) of o-dichlorobenzene, in the presence of 6 g (0.81% by weight) of $AlCl_3$, at 100° C. until a density of $D_4^{100} = 1.330$ g/cm$^3$ is reached. The crude product is washed neutral with an aqueous $NaHCO_3$ solution, rinsed with water and dried.

Yield: 792 g of a mixture of 32.5% of o-dichlorobenzene, 19.0% of 1,2,3-trichlorobenzene, 38.2% of 1,2,4-trichlorobenzene, 6.8% of 1,2,3,4-tetrachlorobenzene, 3.2% of 1,2,4,5-tetrachlorobenzene and 0.3% of pentachlorobenzene.

TABLE

| Example No. | o-DCB employed [g] | Catalyst Type | Catalyst Amount [g] | [% by weight] | Temperature [°C.] | Degree of conversion [mols of chlorine / mols of educt] |
|---|---|---|---|---|---|---|
| 1 | 735 | $AlCl_3$ | 6 | 0.81 | 100 | 0.650 |
| 2 | 735 | $AlCl_3$ | 6 | 0.81 | 20 | 0.678 |
| 3 | 735 | $AlCl_3$ | 3 | 0.4 | 50 | 0.692 |
| 4 | 735 | $AlCl_3$ | 6 | 0.81 | 50 | 0.650 |
| 5 | 735 | $AlCl_3$ | 6 | 0.81 | 50 | 0.838 |
| 6 | 1,470 | $AlCl_3$ | 7.4 | 0.5 | 40 | 0.471 |

| Ex- | Yield of crude | Composition of the crude product (% by weight) Trichloro- |

TABLE-continued

| Example No. | product [g] | benzenes o-DCB | benzenes 1,2,3 | benzenes 1,2,4 | Tetrachlorobenzenes 1,2,3,4 | Tetrachlorobenzenes 1,2,4,5 |
|---|---|---|---|---|---|---|
| 1 | 792 | 32.5 | 19.0 | 38.2 | 6.8 | 3.2 |
| 2 | 814 | 29.0 | 21.1 | 43.2 | 5.0 | 1.7 |
| 3 | 825 | 29.5 | 20.2 | 41.8 | 5.8 | 2.3 |
| 4 | 811 | 32.4 | 19.4 | 39.7 | 6.0 | 2.4 |
| 5 | 827 | 17.9 | 20.9 | 46.7 | 10.0 | 4.2 |
| 6 | 1,628 | 49.5 | 15.9 | 31.1 | 2.4 | 0.9 |

Selectivity:

| Example No. | Penta- + hexa- chloro- benzene [%] | Proportion of trichloro- benzenes in the crude product Isomer composition 1,2,3-TCB | Proportion of trichloro- benzenes in the crude product Isomer composition 1,2,4-TCB | 1,2,3-TriClB in % of conversion |
|---|---|---|---|---|
| 1 | 0.3 | 57.2 | 33.2 | 66.8 | 28.1 |
| 2 | — | 64.3 | 32.8 | 67.2 | 29.7 |
| 3 | — | 62.0 | 32.6 | 67.4 | 28.7 |
| 4 | — | 59.1 | 32.8 | 67.2 | 28.7 |
| 5 | 0.3 | 67.6 | 30.9 | 69.1 | 25.5 |
| 6 | — | 47.0 | 33.8 | 66.2 | 30.5 |

| Example No. | Proportion of higher chlorinated benzenes % of crude product | Proportion of higher chlorinated benzenes % of conversion | Yield of 1,2,3-TriClB [g] |
|---|---|---|---|
| 1 | 10.3 | 15.3 | 150.5 |
| 2 | 6.7 | 9.4 | 171.7 |
| 3 | 3.4 | 11.9 | 166.6 |
| 4 | 8.5 | 12.6 | 157.3 |
| 5 | 14.5 | 17.7 | 172.8 |
| 6 | 3.3 | 6.3 | 258.9 |

Definitions:
(1) Degree of conversion =

$$\Sigma \left( \frac{G_i [\%] \cdot A [g] \cdot \Delta n_i}{MW_i [g] \cdot \text{educt [mol]} \cdot 100} \right)_n \frac{\text{mols of chlorine}}{\text{mols of educt}}$$

i: stage of chlorination (e.g. trichloro-benzene, tetrachloro-benzene)
$G_i$: content of compound i in the crude product (% by weight)
A: total yield (g)
$n_i$: number of chlorine atoms which i contains in excess of those present in the educt (mol)
$MW_i$: molecular weight of i
this accordingly indicates the equivalents of chlorine which were introduced, per mol of educt, during the reaction.
(2) Conversion: this indicates the proportion of educt which has been chlorinated.
(3) Yield of 1,2,3-trichlorobenzene: this indicates how much 1,2,3-trichlorobenzene have been produced from 5 mols of o-dichlorobenzene.

What is claimed is:

1. In a process for the preparation of a trichlorobenzene by chlorinating o-dichlorobenzene in the presence of a catalyst, the improvement which comprises employing as the catalyst, a catalyst which comprises aluminum chloride, wherein the catalyst contains 0.01 to 0.1 part by weight of iron or iron chloride per 100 parts by weight of aluminum chloride.

* * * * *